(12) United States Patent
Mauger et al.

(10) Patent No.: US 12,357,816 B2
(45) Date of Patent: Jul. 15, 2025

(54) DYNAMIC CURRENT STEERING

(71) Applicant: Cochlear Limited, Macquarie University (AU)

(72) Inventors: Stefan Jozef Mauger, Macleod (AU); Zachary Mark Smith, Greenwood Village, CO (US)

(73) Assignee: Cochlear Limited, Macquarie University (AU)

( * ) Notice: Subject to any disclaimer, the term of this patent is extended or adjusted under 35 U.S.C. 154(b) by 704 days.

(21) Appl. No.: 17/025,365

(22) Filed: Sep. 18, 2020

(65) Prior Publication Data

US 2021/0069495 A1      Mar. 11, 2021

Related U.S. Application Data

(63) Continuation of application No. 15/009,146, filed on Jan. 28, 2016, now Pat. No. 10,814,126.

(60) Provisional application No. 62/165,261, filed on May 22, 2015.

(51) Int. Cl.
*A61N 1/08*    (2006.01)
*A61N 1/05*    (2006.01)
*A61N 1/36*    (2006.01)

(52) U.S. Cl.
CPC ....... *A61N 1/0541* (2013.01); *A61N 1/36038* (2017.08)

(58) Field of Classification Search
CPC .................. A61N 1/0541; A61N 1/36032
See application file for complete search history.

(56) References Cited

U.S. PATENT DOCUMENTS

| | | | |
|---|---|---|---|
| 6,052,624 A | 4/2000 | Mann | |
| 6,393,325 B1 | 5/2002 | Mann et al. | |
| 7,082,332 B2 | 7/2006 | Blamey et al. | |
| 8,452,414 B2 | 5/2013 | Poletto | |
| 2004/0158170 A1 | 8/2004 | Overstreet | |
| 2006/0247735 A1* | 11/2006 | Honert | A61N 1/323 607/57 |
| 2007/0156202 A1 | 7/2007 | Zierhofer | |
| 2009/0036962 A1 | 2/2009 | Zierhofer | |
| 2009/0118787 A1* | 5/2009 | Moffitt | A61N 1/36082 607/45 |

(Continued)

FOREIGN PATENT DOCUMENTS

| | | |
|---|---|---|
| CN | 102256663 A | 11/2011 |
| WO | 02/09808 A1 | 2/2002 |

(Continued)

OTHER PUBLICATIONS

Official Communication in counterpart European Application No. 16799437.5-1126, mailed Jun. 14, 2022, 6 pages.

(Continued)

*Primary Examiner* — Michael J D'Abreu
(74) *Attorney, Agent, or Firm* — Edell, Shapiro & Finnan, LLC

(57) ABSTRACT

Presented herein are dynamic current steering techniques in which a dynamic stimulation pulse is delivered to a recipient as current stimulation applied across a plurality of stimulation channels. The current stimulation is weighted and applied in a pattern that results in a time varying progressive change in the location of a locus of the current stimulation across the plurality of channels.

19 Claims, 13 Drawing Sheets

(56) References Cited

U.S. PATENT DOCUMENTS

| | | |
|---|---|---|
| 2009/0312820 A1 | 12/2009 | Nie |
| 2011/0218593 A1 | 9/2011 | Rubinstein |
| 2013/0172956 A1* | 7/2013 | Goddard ............ A61N 1/37241 607/59 |
| 2014/0074214 A1 | 3/2014 | Raje |
| 2015/0025596 A1 | 1/2015 | Kals |
| 2015/0117690 A1 | 4/2015 | Mauger |

FOREIGN PATENT DOCUMENTS

| | | |
|---|---|---|
| WO | 2012024441 A2 | 2/2012 |
| WO | 2013/186743 A2 | 12/2013 |
| WO | 2014/114337 A1 | 7/2014 |
| WO | 2014/135203 A1 | 9/2014 |
| WO | 2014/209287 A1 | 12/2014 |

OTHER PUBLICATIONS

Loeb, et al., "Spatial Cross-Correlation," Biological Cybernetics 47, No. 3, Jul. 1983, pp. 149-163.
Loeb, Gerald, "Are Cochlear Implant Patients Suffering From Perceptual Dissonance?," Ear & Hearing, Copyright ® 2005 by Lippincott Williams & Wilkins, Oct. 2005, pp. 435-450.

* cited by examiner

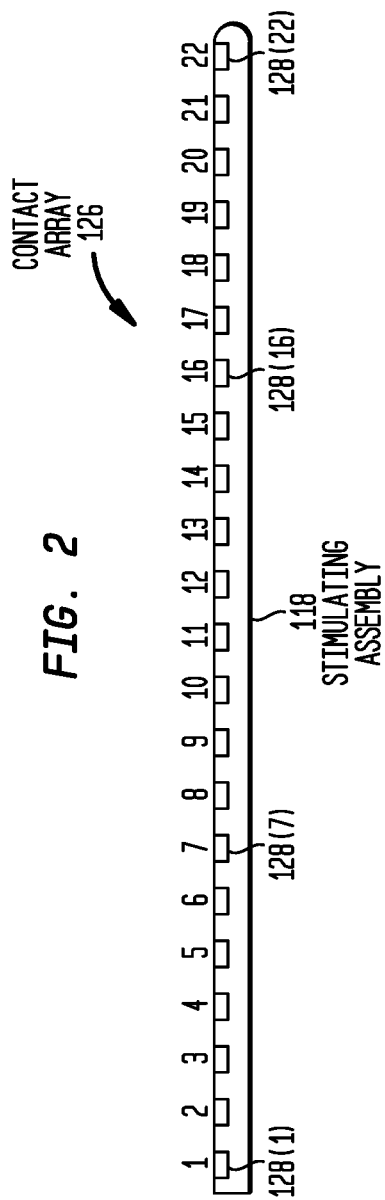

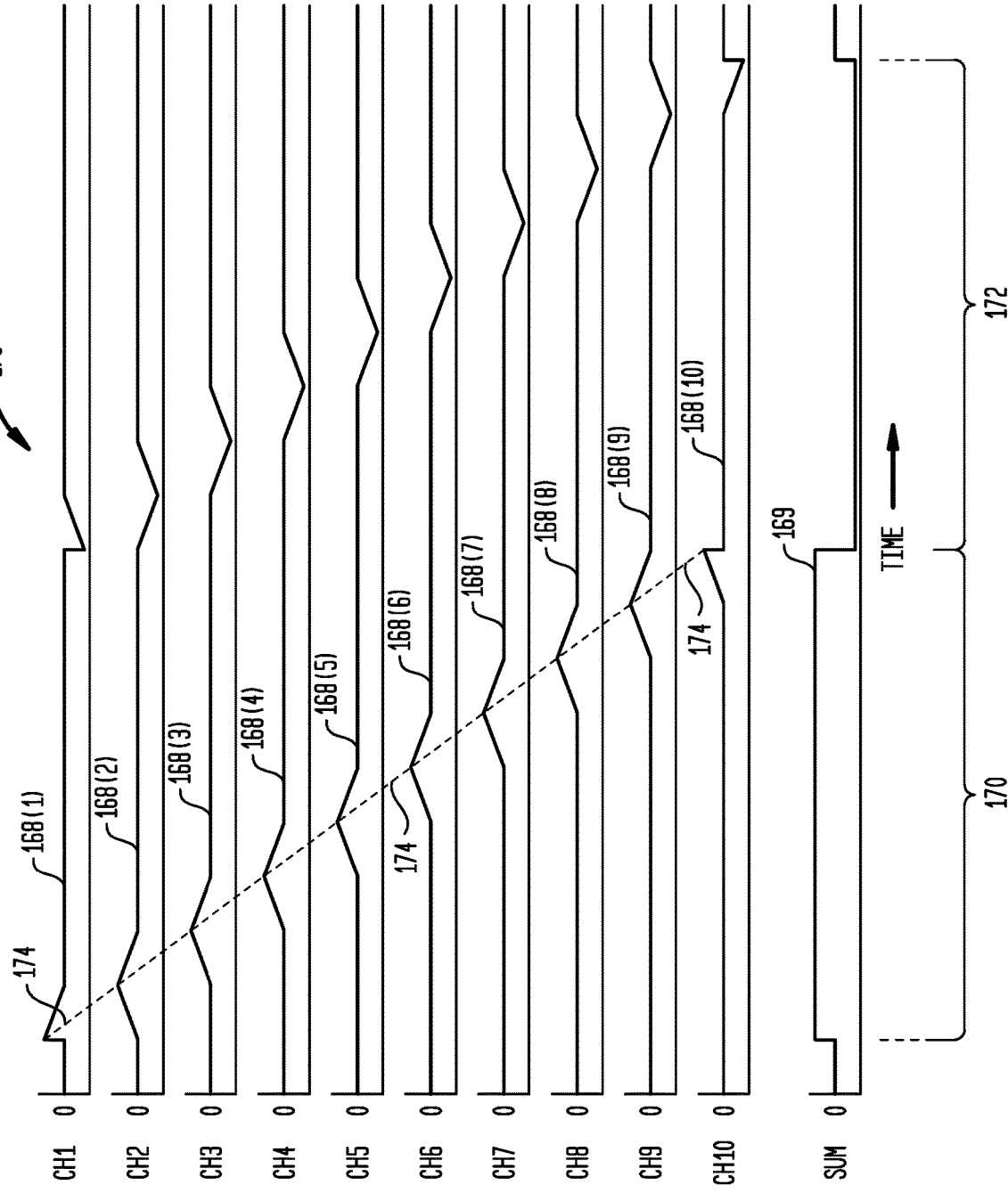

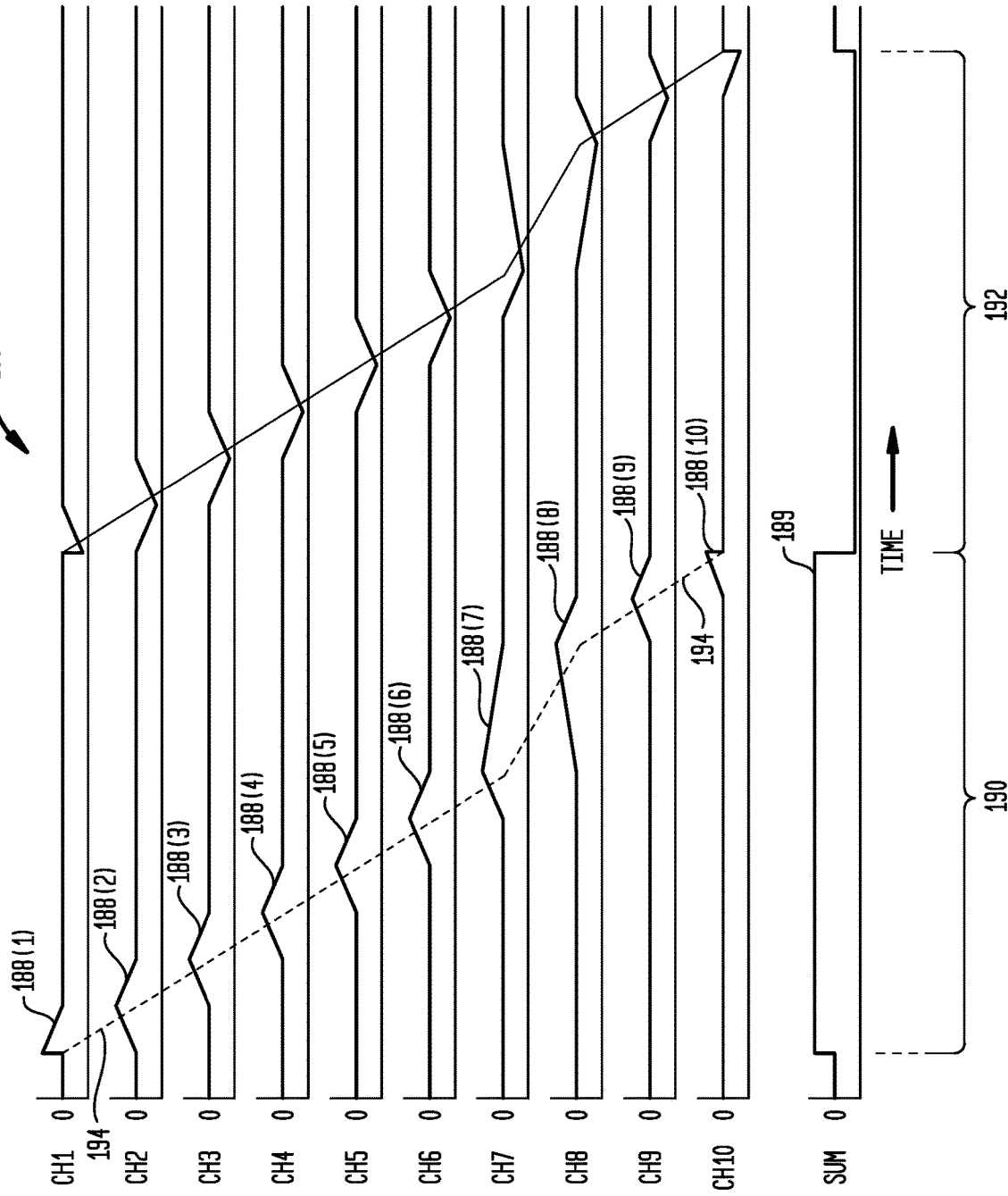

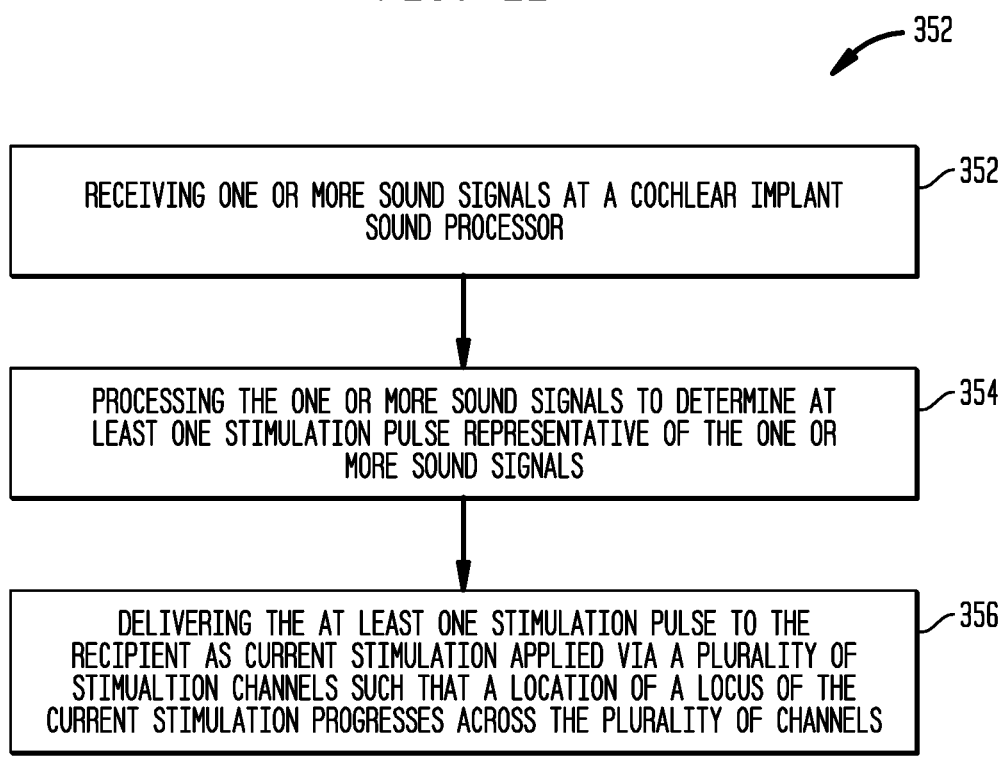

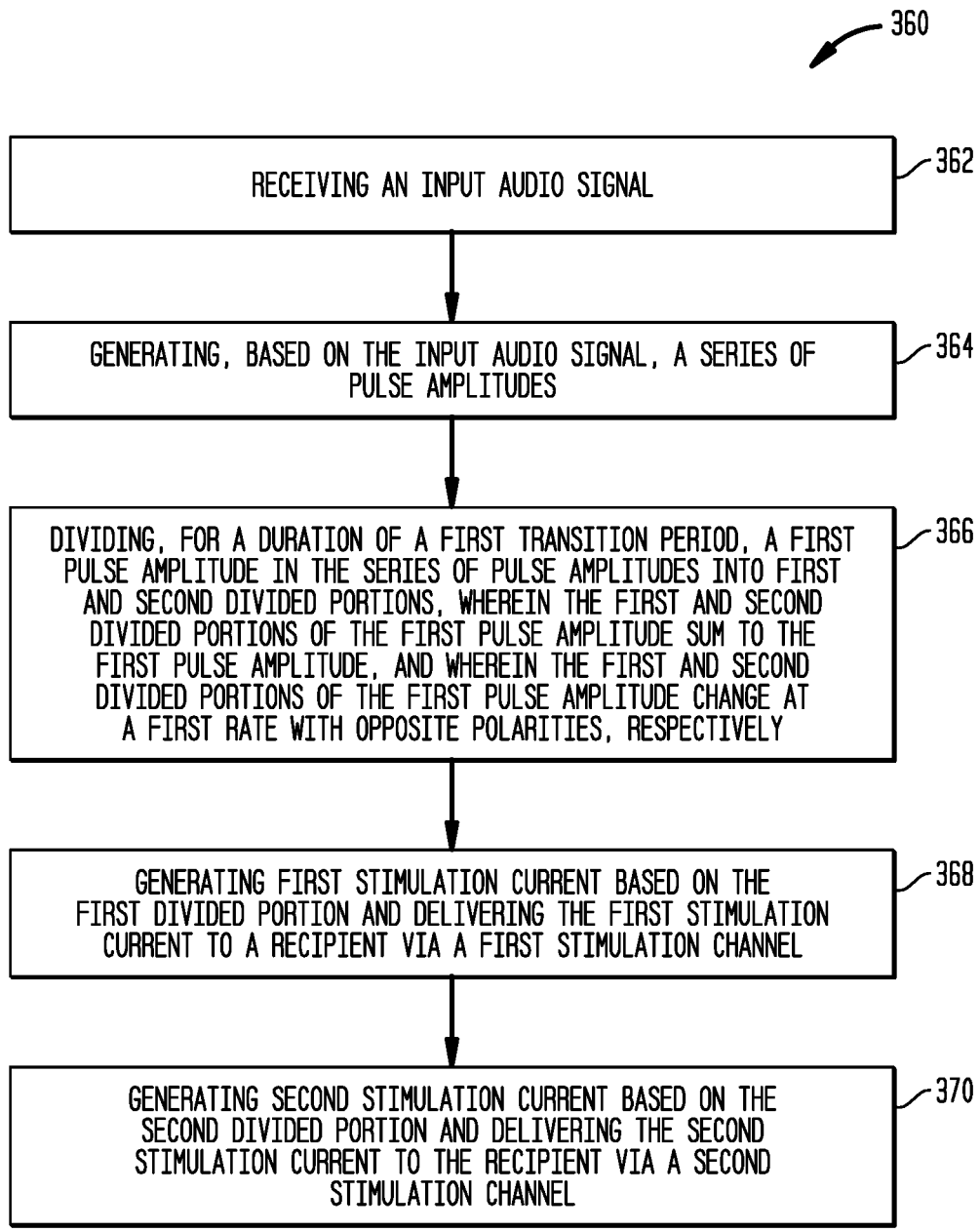

DYNAMIC CURRENT STEERING

CROSS-REFERENCE TO RELATED APPLICATIONS

This application is a continuation of U.S. application Ser. No. 15/009,146 entitled "Dynamic Current Steering", filed Jan. 28, 2016, which claims priority to U.S. Provisional Application No. 62/165,261 entitled "Dynamic Current Steering," filed May 22, 2015, the content of which is hereby incorporated by reference herein.

BACKGROUND

Field of the Invention

The present invention relates generally to tissue-stimulating prostheses.

Related Art

There are several types of medical devices that operate by delivering electrical (current) stimulation to the nerves, muscle or other tissue fibers of a recipient. These medical devices, referred to herein as tissue-stimulating prostheses, typically deliver current stimulation to compensate for a deficiency in the recipient. For example, tissue-stimulating hearing prostheses, such as cochlear implants, are often proposed when a recipient experiences sensorineural hearing loss due to the absence or destruction of the cochlear hair cells, which transduce acoustic signals into nerve impulses. Auditory brainstem stimulators are another type of tissue-stimulating hearing prostheses that might be proposed when a recipient experiences sensorineural hearing loss due to damage to the auditory nerve.

SUMMARY

In one aspect presented herein, a method is provided. The method comprises: receiving one or more sound signals at a hearing prosthesis system; processing the one or more sound signals to determine at least one stimulation pulse representative of the one or more sound signals; and delivering the at least one stimulation pulse to the recipient as current stimulation applied via a plurality of stimulation channels such that a location of a locus of the current stimulation progresses over time across the plurality of stimulation channels.

In another aspect presented herein, a tissue-stimulating prosthesis system is provided. The tissue-stimulating prosthesis system comprises: one or more sound input elements configured to receive a sound signal; a sound processor configured to generate one or more processed signals representative of the sound signal; a plurality of stimulation channels each terminating at one or more electrical stimulating contacts implanted in a cochlea of a recipient; and a stimulator unit configured to simultaneously generate, based on at least one of the one or more processed signals, overlapping time varying current fields across two or more of the stimulation channels that collectively cause a time varying change in a locus of the overlapping current fields.

In another aspect a method is provided. The method comprises: receiving an input audio signal; generating, based on the input audio signal, a series of pulse amplitudes; dividing, for a duration of a first transition period, a first pulse amplitude in the series of pulse amplitudes into first and second divided portions, wherein the first and second divided portions of the first pulse amplitude sum to the first pulse amplitude, and wherein the first and second divided portions of the first pulse amplitude change at a first rate with opposite polarities, respectively; generating first stimulation current based on the first divided portion and delivering the first stimulation current to a recipient via a first stimulation channel; and generating second stimulation current based on the second divided portion and delivering the second stimulation current to the recipient via a second stimulation channel.

In another aspect a method is provided. The method comprises: receiving a sound signal at a hearing prosthesis system; processing the sound signal to determine at least one dynamic stimulation pulse representative of the sound signal; and delivering the at least one dynamic stimulation pulse to the recipient in a weighted spatial-temporal pattern that results in a time varying progressive change in a location of a locus of current stimulation across a plurality of stimulation channels.

BRIEF DESCRIPTION OF THE DRAWINGS

Embodiments of the present invention are described herein in conjunction with the accompanying drawings, in which:

FIG. 2 is a schematic diagram of an intra-cochlear stimulating assembly configured for use in accordance with embodiments presented herein;

FIG. 5 is a plot illustrating an example in which ten stimulation channels are used to deliver a biphasic dynamic stimulation pulse having the same amplitude across all ten channels, in accordance with embodiments presented herein;

FIG. 8 is a plot illustrating a dynamic stimulation pulse having a varying velocity in accordance with embodiments presented herein;

FIG. 11 is a high-level flowchart of a dynamic current steering method in accordance with embodiments presented herein; and FIG. 12 is a high-level flowchart of a dynamic current steering method in accordance with embodiments presented herein.

DETAILED DESCRIPTION

Presented herein are dynamic current steering techniques in which a dynamic stimulation pulse is delivered to a recipient as current stimulation applied across a plurality of stimulation channels. The current stimulation is weighted and applied in a pattern that results in a progressive time-varying change in the location of a locus of the current stimulation across the plurality of channels.

As noted, there are several types of tissue-stimulating prostheses that deliver stimulation to compensate for a deficiency in a recipient. Merely for ease of illustration, the dynamic current steering techniques presented herein are primarily described herein with reference to one type of tissue-stimulating prosthesis, namely a cochlear implant. It is to be appreciated that the dynamic current steering techniques presented herein may be used with other tissue-stimulating prostheses including, for example, auditory brainstem stimulators, implantable pacemakers, defibrillators, functional electrical stimulation devices, pain relief stimulators, visual prostheses, other neural or neuromuscular stimulators, etc.

Figure 1:
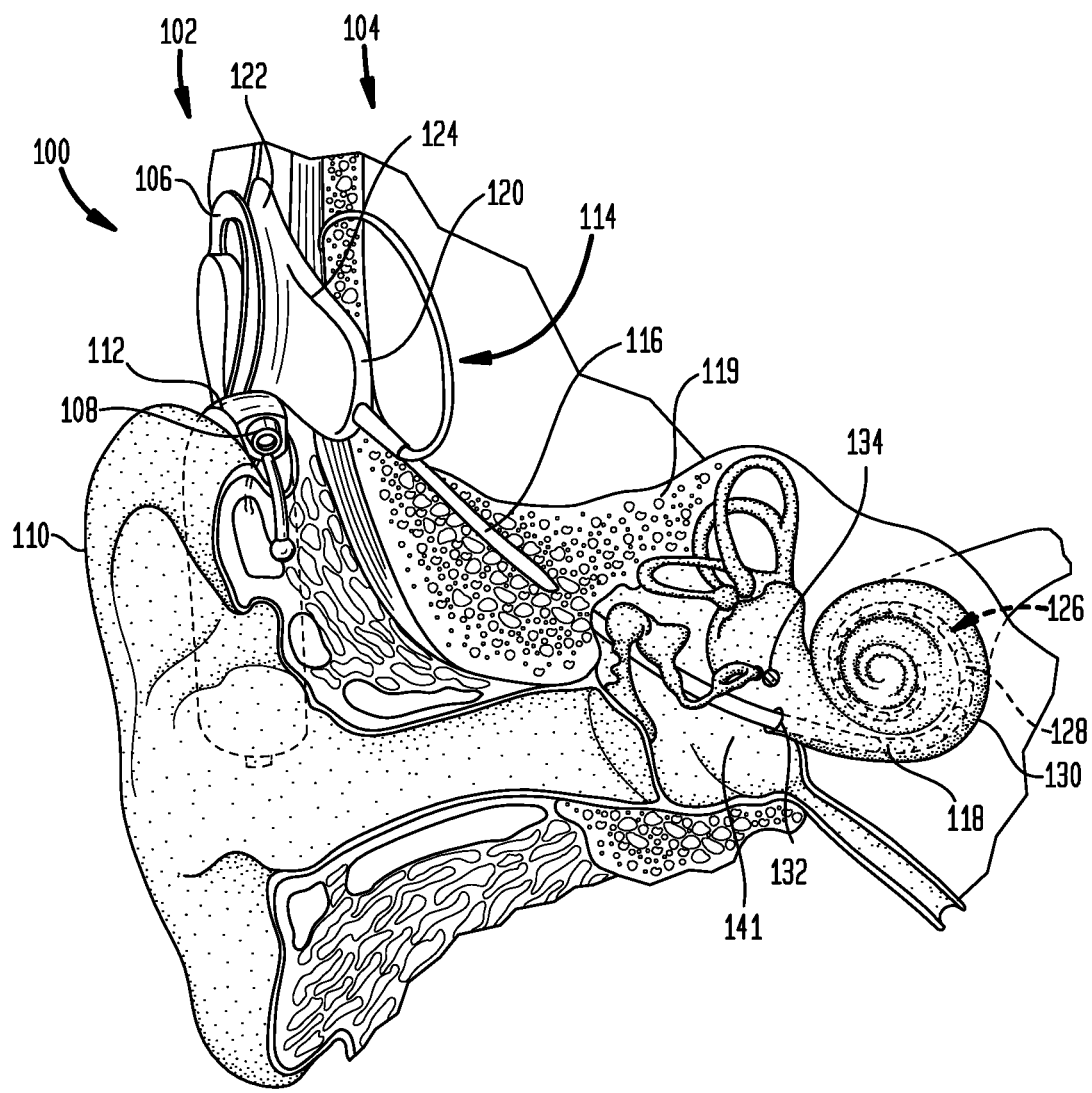
FIG. 1 is a schematic diagram of a cochlear implant system configured for use in accordance with embodiments presented herein.

FIG. 1 is perspective view of an exemplary cochlear implant system 100 that is configured to execute the dynamic current steering in accordance with embodiments presented herein. The cochlear implant system 100 includes an external component 102 and an internal/implantable component 104. The external component 102 is directly or indirectly attached to the body of the recipient and typically comprises an external coil 106 and, generally, a magnet (not shown in FIG. 1) fixed relative to the external coil 106. The external component 102 also comprises one or more sound input elements 108 (e.g., microphones, telecoils, etc.) for detecting sound signals or input audio signals, and a sound processing unit 112. The sound processing unit 112 includes, for example, a power source (not shown in FIG. 1) and a sound processor (also not shown in FIG. 1). The sound processor is configured to process electrical signals generated by a sound input element 108 that is positioned, in the depicted embodiment, by auricle 110 of the recipient. The sound processor provides the processed signals to external coil 106 via, for example, a cable (not shown in FIG. 1).

The implantable component 104 comprises an implant body 114, a lead region 116, and an elongate intra-cochlear stimulating assembly 118. The implant body 114 comprises a stimulator unit 120, an internal/implantable coil 122, and an internal receiver/transceiver unit 124, sometimes referred to herein as transceiver unit 124. The transceiver unit 124 is connected to the implantable coil 122 and, generally, a magnet (not shown) fixed relative to the internal coil 122.

The magnets in the external component 102 and implantable component 104 facilitate the operational alignment of the external coil 106 with the implantable coil 122. The operational alignment of the coils enables the implantable coil 122 to transmit/receive power and data to/from the external coil 106. More specifically, in certain examples, external coil 106 transmits electrical signals (e.g., power and stimulation data) to implantable coil 122 via a radio frequency (RF) link. Implantable coil 122 is typically a wire antenna coil comprised of multiple turns of electrically insulated single-strand or multi-strand platinum or gold wire. The electrical insulation of implantable coil 122 is provided by a flexible molding (e.g., silicone molding). In use, transceiver unit 124 may be positioned in a recess of the temporal bone of the recipient. Various other types of energy transfer, such as infrared (IR), electromagnetic, capacitive and inductive transfer, may be used to transfer the power and/or data from an external device to a cochlear implant and, as such, FIG. 1 illustrates only one example arrangement.

Elongate stimulating assembly 118 is configured to be at least partially implanted in cochlea 130 and includes a plurality of longitudinally spaced intra-cochlear electrical stimulating contacts (electrical contacts) 128 that collectively form a contact array 126. Stimulating assembly 118 extends through an opening in the cochlea 130 (e.g., cochleostomy 132, the round window 134, etc.) and has a proximal end connected to stimulator unit 120 via lead region 116 that extends through mastoid bone 119. Lead region 116 couples the stimulating assembly 118 to implant body 114 and, more particularly, stimulator unit 120.

In general, the sound processor in sound processing unit 112 is configured to execute sound processing and coding to convert a detected sound into a coded signal corresponding to electrical signals for delivery to the recipient. The coded signal generated by the sound processor is then sent to the stimulator unit 120 via the RF link between the external coil 106 and the internal coil 122. The stimulator unit 120 includes one or more circuits that use the coded signals received via the transceiver unit 124, so as to output stimulation (stimulation current) via one or more stimulation channels that terminate in the stimulating contacts 128. As such, the stimulation is delivered to the recipient via the stimulating contacts 128. In this way, cochlear implant system 100 stimulates the recipient's auditory nerve cells, bypassing absent or defective hair cells that normally transduce acoustic vibrations into neural activity.

FIG. 2 illustrates a more detailed view of a portion of the stimulating assembly 118 of FIG. 1 comprising the array 126 of stimulating contacts 128. FIG. 2 illustrates a specific arrangement in which stimulating assembly 118 comprises twenty-two (22) electrical contacts (electrodes). As such, the electrical contacts are labeled in FIG. 2 as contacts 128(1) through 128(22), where contact 128(1) is the most basal/proximal electrical contact and electrical contact 128(22) is the most distal/apical contact. The stimulating assembly 118 may also include or operate with an extra-cochlear electrode (ECE) that is positioned outside of the recipient's cochlea. For ease of illustration, the extra-cochlear electrode has been omitted from FIGS. 1 and 2.

Because the cochlea is tonotopically mapped, that is, partitioned into regions each responsive to stimulus signals in a particular frequency range, acoustic frequencies are allocated to one or more electrical contacts 128 of the stimulating assembly 118 that are positioned close to the region that would naturally be stimulated in normal (acoustic) hearing. As such, processing channels of the sound processor (i.e., specific frequency bands with their associated signal processing paths) are each mapped to a set of one or more stimulating contacts to stimulate a selected population of cochlea nerve cells, sometimes referred to as target nerve populations or target neurons. Such sets of one or more stimulating contacts for use in stimulation are referred to herein as "stimulation channels." That is, a stimulation channel is made up of a single or multiple electrical contacts stimulated with or without a far field return contact.

In general, conventional cochlear implant stimulation strategies result in the delivery of discrete rectangular biphasic current pulses at fixed locations or fixed spatial profiles over relatively short periods of time (e.g., on a 5 microsecond (μs) to 250 μu timescale). The location or spatial profile varies from pulse to pulse (i.e., stimulation pulses are delivered via one channel, then via another, and so on). For example, the Continuous interleaved sampling (CIS) and advanced combination encoders (ACE) sound coding strategies typically order sequential stimulation pulses from Base to Apex (i.e., stimulation contact 128(1) to 128(22)), or from Apex to Base, and deliver the current pulses spaced sequentially and evenly over time. The main focus of these strategies is to map the input sound signal's channel amplitudes from a range of frequency bands to corresponding channel locations assigned to those frequencies. Sequential pulses are used to avoid any temporal overlap of current from more than one channel since simultaneous stimulation can cause high degrees of interactions between channels and unwanted (and sometimes unknown or uncontrollable) distortions in the level of stimulation.

A single current pulse in a sequential stimulation strategy activates neurons nearest the stimulated (delivery) contact and, due to current spread, additional neurons close to adjacent unstimulated contacts. Resultant neural activation from a single pulse is highly synchronized (time locked) across the affected neural population, with neurons further away from the stimulating contact having slightly longer latencies. Resultant neural activation from a number of sequential pulses is time quantized, with a mixture of neurons at a location being activated from previous pulses on contacts that are not the closest thereto. As such, these neurons may be refraction and may not respond to a subsequent stimuli delivered on the closer contacts. While not ideal, this synchronized and quantized stimulation is able to represent the channel amplitudes well enough for successful speech perception by most cochlear implant recipients. However, this stimulation provides a spatial-temporal representation of the original acoustic signal that is distorted when compared to acoustic hearing.

More specifically, there are approximately 3000 rows of hair cells in the human cochlea. Each row, or position along the length of the cochlea, responds best to a different acoustic frequency (i.e., tonotopic mapping). Since cochlear implants typically have only a limited number of stimulating contacts (e.g., 22 contacts), there is a large underrepresentation of the frequency spectrum during delivery of stimulation when compared to normal acoustic hearing.

Another aspect of acoustic hearing is that acoustic stimulation is a continuous analog process (i.e., a traveling wave), rather than a series of discrete stimulations. That is, sound waves enter the cochlear fluid at the oval window and travel from the base to the apex of the cochlear in a continuous motion. Accordingly, the delivery of discrete and sequential pulses is unable to represent the rich spatial-temporal patterns of acoustic hearing. For example, slow continuous transitions along the cochlea (>10 milliseconds (ms)) are not well represented by short sequential current pulses (~100 μs) that start with a peak response.

As such, presented herein are techniques for delivering dynamic stimulation pulses to a cochlear implant recipient. As used herein, a "dynamic stimulation pulse" refers to current stimulation that is weighted and delivered in a spatial-temporal pattern that results in a perceptible progressive change in the location of a locus of the current stimulation across the plurality of channels. That is, dynamic current steering techniques are proposed to steadily move the locus of excitation over time so as to more closely mimic features of the acoustic traveling wave and/or to mimic other dynamic features (e.g., ensemble codes).

Figure 3A:
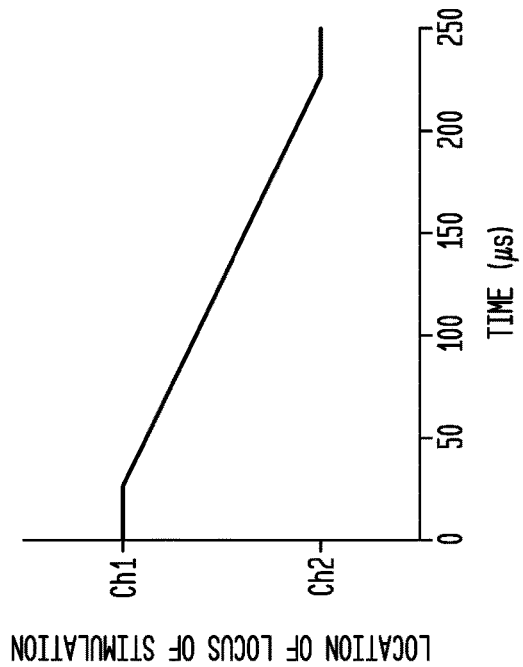
FIGS. 3A-3D are plots illustrating a simplified implementation of the dynamic current steering techniques presented herein.
Figure 3B:
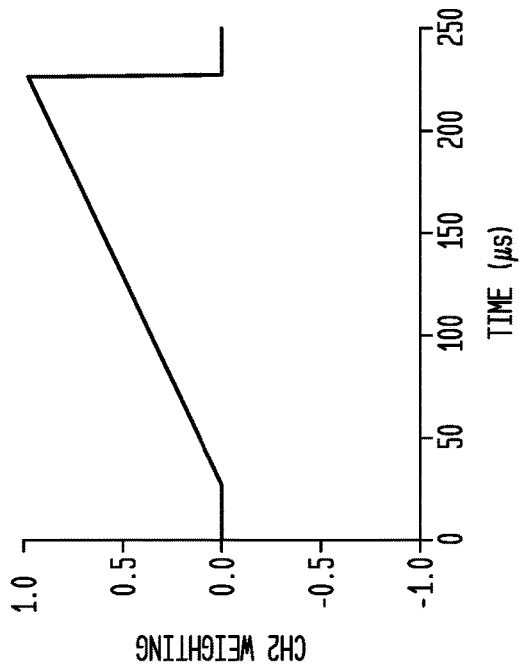

FIGS. 3A-3D are plots illustrating an implementation of the dynamic current steering techniques presented herein. More specifically, FIG. 3A illustrates a monophasic pulse 150 that is delivered to a recipient as a dynamic stimulation pulse sliding (progressively moving) across two stimulation channels. The dynamic stimulation pulse in the example of FIGS. 3A-3D starts at a first stimulation channel (channel 1 (Ch1)) and ends at a second stimulation channel (channel 2 (Ch2)) with the location of the current locus moving in time from one location to another. FIG. 3B illustrates the time-varying the change in the locus of the stimulation between the first and second stimulation channels. In general, the change in the locus of stimulation is achieved by simultaneously delivering stimulation at the first and second channels while dynamically changing the weighting between each channel over time according to the desired location of stimulation.

Figure 3C:
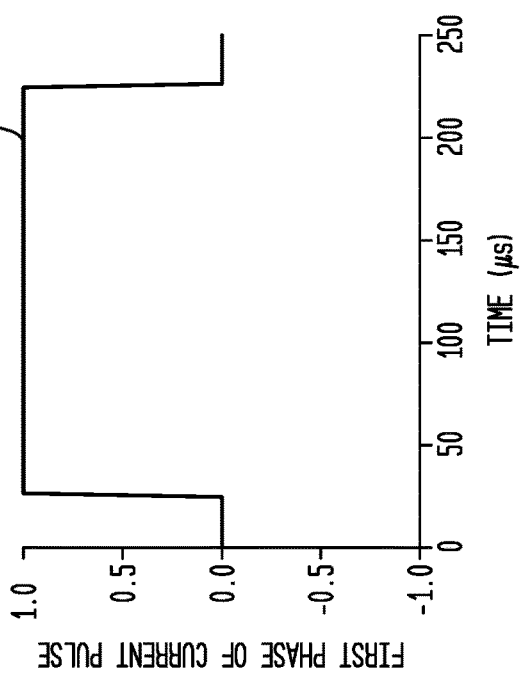
Figure 3D:
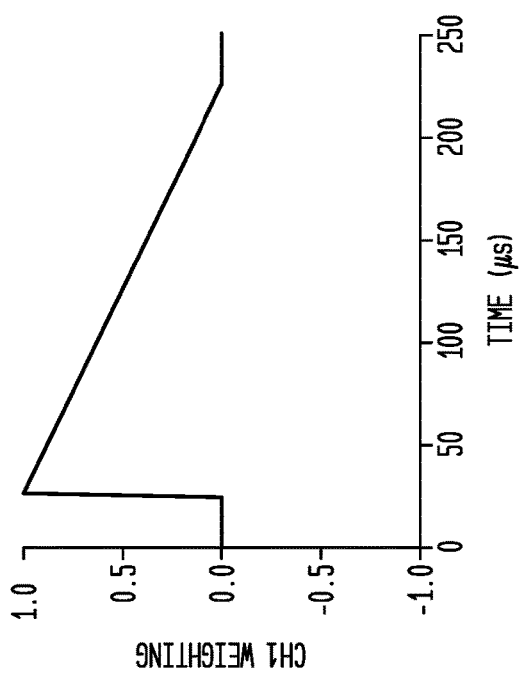

FIG. 3C illustrates the current weighting applied to channel 1, while FIG. 3D illustrates the current weighting applied to channel 2. FIGS. 3C and 3D illustrate the weighting of channels 1 and 2 with reference to the same time scale, thereby making it clear that the weighted stimulation is applied simultaneously at the two channels. The same time scale is also used in FIG. 3B to illustrate how the weightings, when applied simultaneously, move the locus of stimulation form channel 1 to channel 2.

More specifically, FIG. 3C illustrates that a weighting of "1" is initially applied at channel 1, while a weighting of "0" is initially applied at channel 2. The weightings at channels 1 and 2 change in an inverse linear manner (i.e., the weighting applied at channel 1 linearly decreases from 1 to 0, while the weighting applied at channel 2 linearly increases from 0 to 1). This leads to the general change in the locus of stimulation shown in FIG. 3B.

Due to fact that charge balance is often an important aspect of electric stimulation of neural tissue, the use of biphasic current pulses is widespread. Additionally, since neural excitation is achieved primarily by the first phase of a biphasic current pulse, certain aspects presented herein move the location of the stimulation locus of a first phase (positive phase) only. However, in order to maintain charge balance, in certain examples the first phase is repeated, but with an opposite polarity.

FIG. 3A, above, represents a pulse amplitude that may be generated, for example, based on an input audio signal. FIG. 3B illustrates a time period, sometimes referred to herein as a "transition period," in which the location of the locus of the current stimulation transitions or moves from channel 1 to channel 2. Therefore, as generally represented by the current weightings of FIGS. 3C and 3D, during the transition period the pulse amplitude of FIG. 3A is divided into first and second portions. At any point in time during the transition period, the first and second divided portions sum to the pulse amplitude of FIG. 3A. Additionally, the first and second divided portions change at a first rate (represented by slopes of the lines in FIGS. 3C and 3D) with opposite polarities. FIGS. 3C and 3D illustrate an example in which the rate of change of the first and second divided portions is constant. In other examples, the first rate may be variable. In operation, a first stimulation current is generated based on the first divided portion and this first stimulation current is delivered to the recipient via channel 1. Similarly, a second stimulation current is generated based on the second divided portion and is delivered to the recipient via channel 2. Channels 1 and 2 may be adjacent or separated by one or more other channels.

Figure 4A:
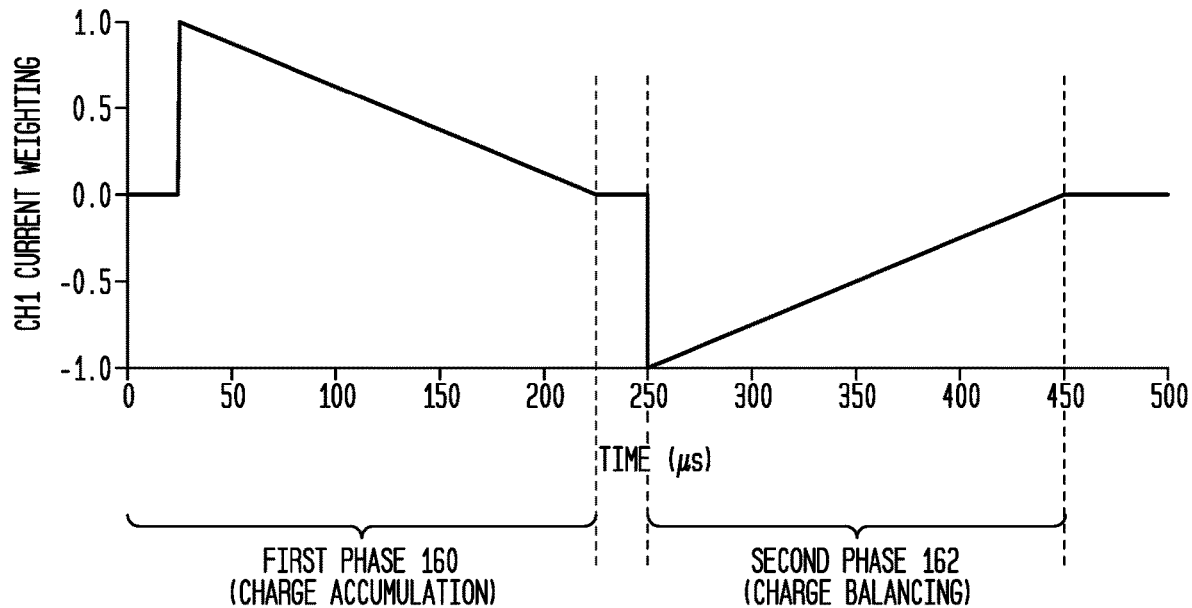
FIGS. 4A and 4B are plots illustrating the delivery of two opposite pulse phases for charge balancing in accordance with embodiments presented herein.
Figure 4B:
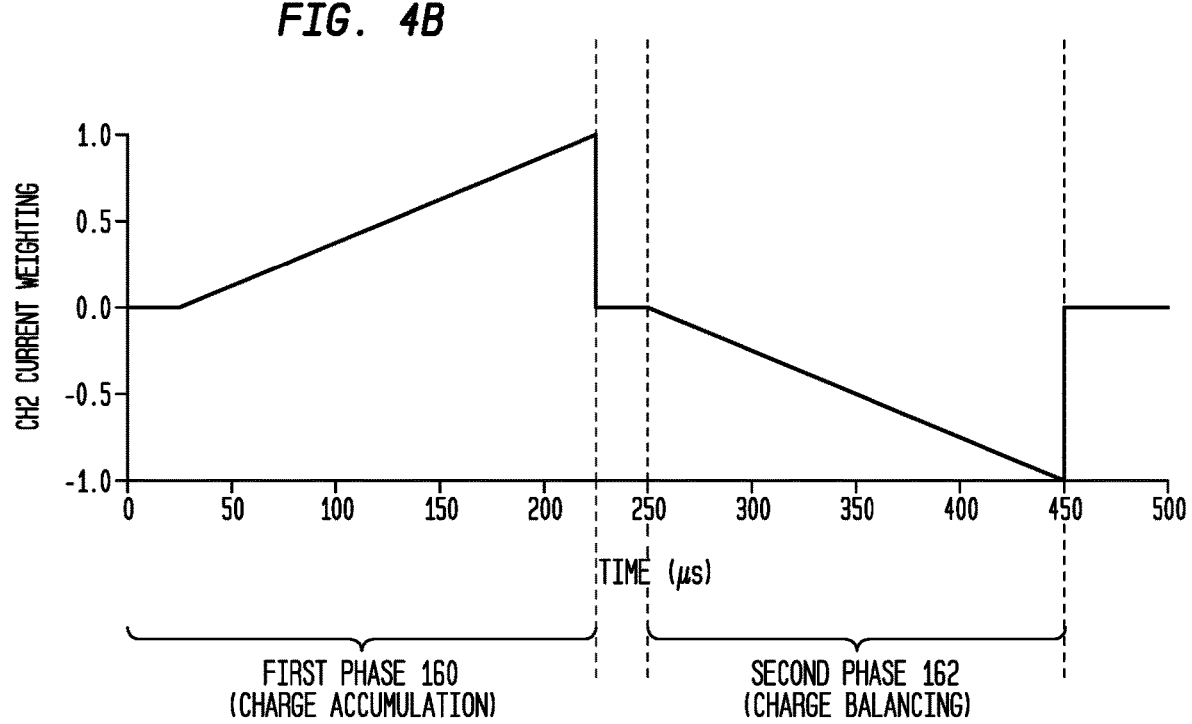

FIGS. 4A and 4B are schematic diagrams illustrating the delivery of two opposite pulse phases for charge balancing.

More specifically, FIG. 4A illustrates the current weighting applied to channel 1, while FIG. 4B illustrates the current weighting applied to channel 2 with reference to the same time scale. As shown, the biphasic dynamic stimulation pulse in this embodiment is formed by applying positive weightings (positive current) to the first and second channels during the first phase (charge accumulation phase) 160 and by applying negative weightings (negative currents) during the second phase (charge balancing phase) 162. As such, the locations of charge accumulation and charge reversal repeat one another (i.e., recouping charge directly after the first phase by repeating it with the opposite polarity during the second phase).

It is to be appreciated that there are a number of other techniques that may be used to recoup charge and the use of a biphasic dynamic stimulation pulse is merely one example method thereof. In other examples, a dynamic stimulation pulse may be applied across a plurality of stimulating channels in a first direction and then a second dynamic stimulation pulse, with an opposite polarity, may be applied across the plurality of stimulation channels in an opposite direction. For example, the first dynamic stimulation pulse is applied to travel in a distal direction (i.e. from basal to apical), while the second dynamic stimulation pulse is applied to travel in a proximal direction (i.e., from apical to basal). In other examples, flat discharge pulses or non-symmetric stimulation and discharge pulses may be applied. Other charge balancing methods are possible and may be used as part of the techniques presented herein.

As noted, FIGS. 3A-3D and 4A-4B illustrate an example in which a dynamic stimulation pulse is applied across (i.e., slides across) two stimulation channels. In practice, it is likely that a dynamic stimulation pulse would be applied across a greater number of stimulation channels. For example, FIG. 5 illustrates an example in which ten (10) contiguous channels are used to deliver a biphasic dynamic stimulation pulse having the same amplitude across all ten channels. More specifically, FIG. 5 includes ten traces 168(1)-168(10) that each illustrate the current waveforms for each of channel 1 (Ch1) through channel 10 (Ch10), respectively, with increasing time. As shown by dashed line 174, the locus of peak current in this example smoothly moves from channel 1 through channel 10, sweeping though all of the channels in between. Therefore, the collective traces 168(1)-168(10) represent the delivered dynamic stimulation pulse 175 as a series ramped and damped current segments.

FIG. 5 also includes a trace 169 representing the sum of the currents from traces 168(1)-168(10). Similar to the arrangement of FIGS. 4A and 4B, since the dynamic stimulation pulse 175 of FIG. 5 is biphasic, the dynamic current pulse generally is comprised of a charge accumulation phase 170 followed by a subsequent charge balancing phase 172 (i.e., positive phase sweep followed by a negative single phase sweeping across the ten stimulation channels).

Figure 6A:
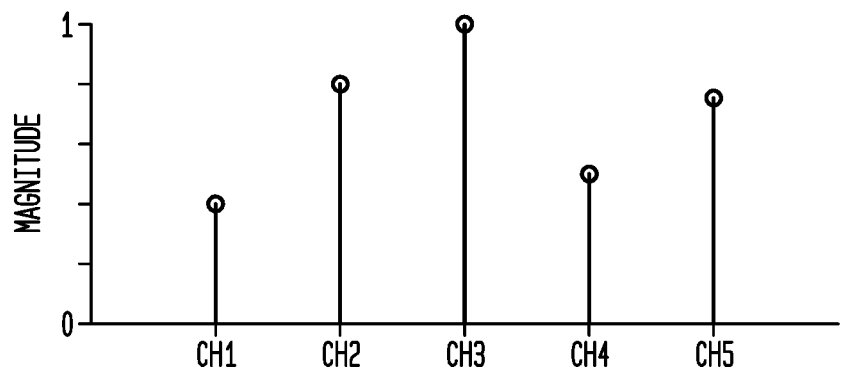
FIGS. 6A and 6B are plots illustrating an example in which current amplitudes of a dynamic stimulation pulse vary across different stimulation channels, in accordance with embodiments presented herein.
Figure 6B:
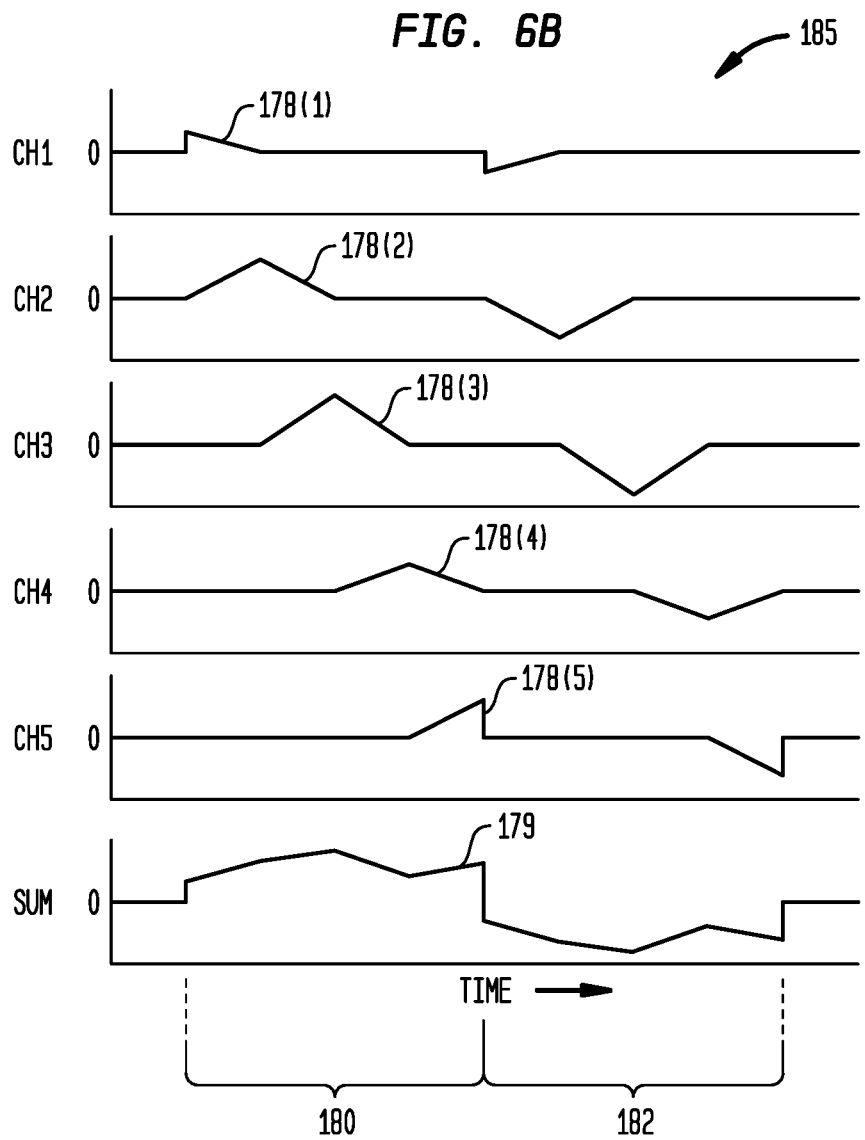

The examples of FIGS. 3A-3D, 4A-4B, and 5 illustrate dynamic stimulation pulses having equal peak current amplitudes at each stimulation channel and a fixed total current level throughout the duration of the dynamic stimulation pulse (e.g., as seen in the sum of FIG. 5). In practice, current amplitudes applied in a cochlear implant are not equal, but rather vary according to the short-term spectrum (intensity versus frequency) of an incoming acoustic sound signal and according to the currents required to elicit the corresponding perceptual loudness in the recipient at a particular location in the cochlea (i.e., loudness variations due to neural survival, anatomical variations, etc. FIGS. 6A and 6B illustrate an example in which current amplitudes vary between electrodes and throughout a dynamic stimulation pulse across a number of electrodes.

More specifically, FIG. 6A illustrates five input magnitudes each corresponding to one of five channels Ch1 to Ch5. The input magnitudes are generated, for example, from the short-time frequency spectrum of an incoming acoustic sound signal. FIG. 6B includes five traces 178(1)-178(5) corresponding to current outputs for each of the five channels shown in FIG. 6A, as well as a trace 179 illustrating the current sum of all five channels. In FIG. 6B, the peak current of each channel is scaled by the corresponding input magnitude shown in FIG. 6A. As shown by trace 179, each phase of the summed currents follows the shape of the input magnitudes (from left to right). That is, the delivered current amplitudes dynamically vary based on the acoustic signal magnitude at the corresponding frequency location.

The embodiment of FIGS. 6A and 6B illustrates the scaling of the channel currents according to the input frequency spectrum only. However, an additional scaling may also be performed to put the currents into the right range for perception as designated in the clinical "map" parameters set by a clinician/audiologist. This is commonly known in the field and is sometimes referred to as current mapping.

Similar to the above examples, in FIG. 6B the locus of peak current stimulation smoothly moves from Ch1 through Ch5, sweeping though all of the channels in between. Therefore, the collective traces 178(1)-178(5) represent the delivered dynamic stimulation pulse 185 as a series ramped and damped current segments. Also similar to the above examples, since the dynamic stimulation pulse 185 of FIG. 6B is biphasic, the dynamic current pulse is generally comprised of a charge accumulation phase 180 followed by a subsequent charge balancing phase 182 (i.e., positive phase sweep followed by a negative single phase sweeping across the five stimulation channels). In each phase 180 and 182, the applied currents are the inverse of one another.

In FIGS. 6A and 6B, the current amplitudes of the dynamic stimulation pulse vary/adjust at the stimulation channels Ch1 to Ch5. In a further embodiment, greater control may be exercised to vary the current amplitude of a dynamic stimulation pulse at locations at, not only each stimulation channel, but also at locations between stimulation channels. That is, the delivered current may be varied according to changes in desired amplitude at locations in-between physical stimulation channels. An example of such an embodiment is shown in FIGS. 7A-7H. For ease of illustration, FIGS. 7A-7H illustrate an embodiment in which only two channels are used to code amplitudes at the two stimulation channels and in between the two stimulation channels.

Figure 7A:
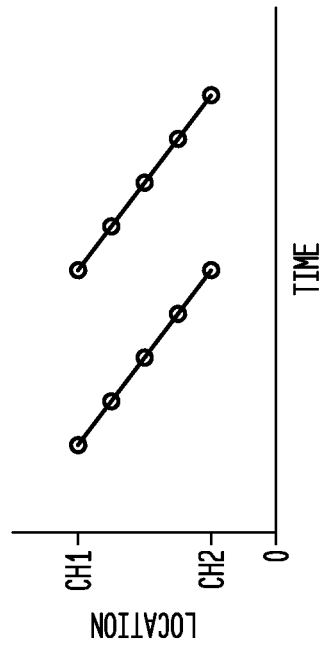
FIGS. 7A-7H are plots illustrating an embodiment in which multiple current amplitudes are encoded between stimulation channels in accordance with embodiments presented herein.

FIG. 7A illustrates five input magnitudes generated for Ch1 and Ch2, where there is one input magnitude for each stimulation channel and three middle input magnitudes located in-between Ch1 and Ch2. Again, the five input magnitudes shown in FIG. 7A may be generated, for example, from the short-time frequency spectrum of an incoming acoustic sound signal.

Figure 7B:
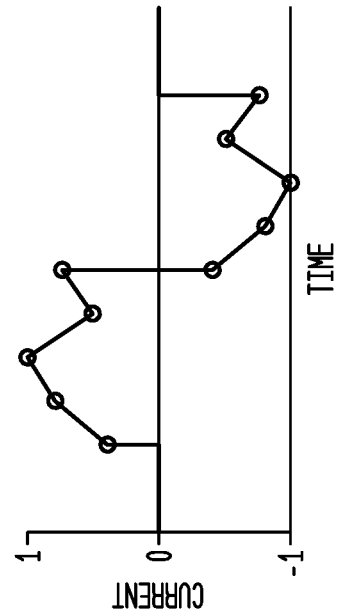
Figure 7C:
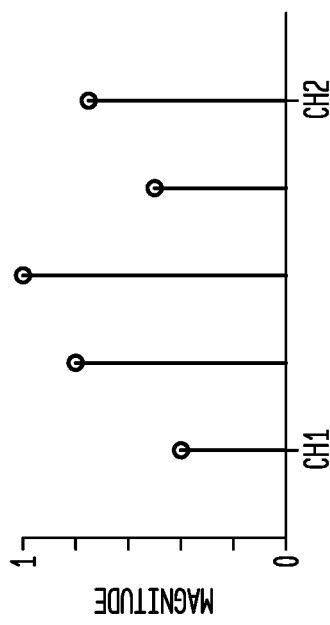
Figure 7D:
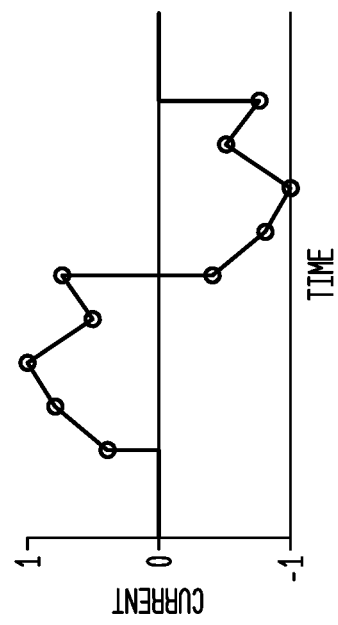
Figure 7E:
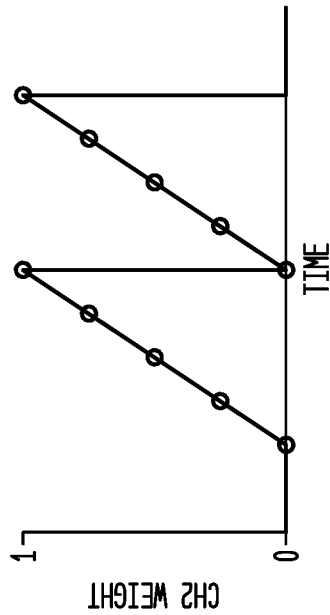
Figure 7F:
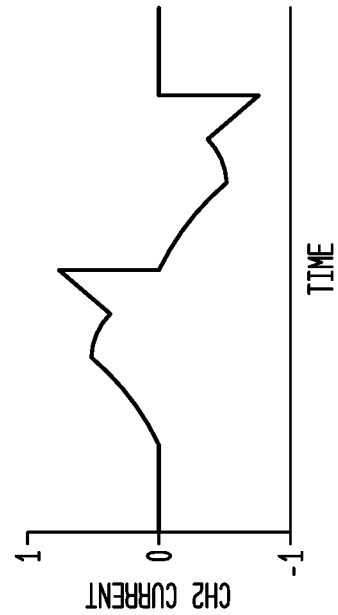
Figure 7G:
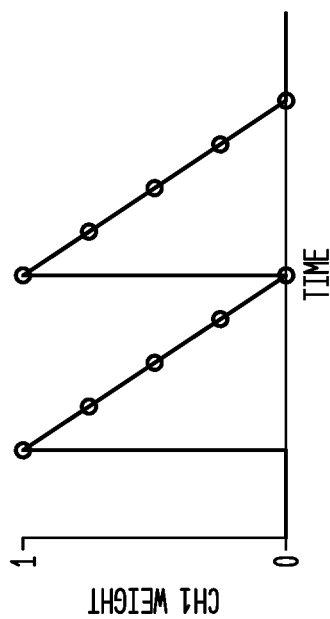
Figure 7H:
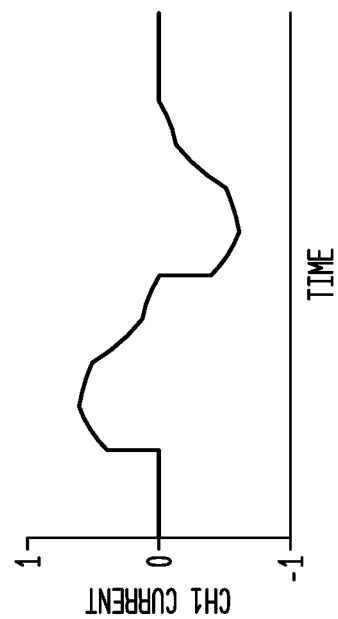

As shown in FIG. 7B, for a biphasic dynamic stimulation pulse example, two stimulation sweeps from Ch1 to Ch2 are used to represent the first and second phases of the biphasic pulse. The input current waveforms, shown in FIGS. 7C and 7D, are biphasic and scaled by the corresponding acoustic input magnitudes shown in FIG. 7A. The input current waveforms for each channel are then weighted by their corresponding current weightings, shown in FIGS. 7E and 7F, to obtain a dynamic stimulation pulse. The final output currents are shown in FIGS. 7G and 7H for Ch1 and Ch2, respectively. The final output of FIGS. 7G and 7H are obtained by multiplying the input currents of FIGS. 7C and 7D with the dynamic weights (dynamic current steering gains) of FIGS. 7E and 7F, respectively. As shown, the waveforms of FIGS. 7G and 7H are continuously varying and are not necessarily piecewise linear. Also, as before, the currents may be mapped into the correct perceptual range for the patient by mapping the input currents to the correct range that elicits sounds in the correct perceptual loudness range.

As noted, FIGS. 7A-7H illustrate a dynamic stimulation pulse delivered across two channels in order to obtain current variations a locations between the two channels. It is to be appreciated that the technique of FIGS. 7A and 7H can be can be extended across several (i.e. more that two) channels so as to create more continuous coding of stimulus amplitude across the cochlea that is unconstrained by the number of physical channels.

In acoustic hearing, the acoustic traveling wave moves distally/apically from the basal end of the cochlea towards the characteristic frequency of the stimulus. For example, a pure tone enters the cochlea at the oval window and initiates a pressure wave that travels along the length of the cochlea. The amplitude of the wave peaks at the tonotopic location corresponding to the characteristic frequency of the tone and decreases rapidly past this location. The velocity of the traveling wave also slows down near the characteristic frequency. For harmonic tone complexes, which elicit a strong musical pitch, resolved harmonics also slow down at their corresponding characteristic frequencies. Besides creating a peak in the response at each characteristic frequency, local phase differences increase at these places and may be an essential cue for musical pitch perception. In electrical hearing, dynamic stimulation pulses can be modified to reproduce or mimic the variations in the velocity of the acoustic traveling wave. This may be useful in recreating strong musical pitch with electric hearing, which to date has been an unsolved challenge.

As shown below in Equation 1, the velocity of a dynamic stimulation pulse, $v_{electric}$, is a function of the duration of each ramped and damped segment of the triangular pulse shapes, $t_{ramp}$, and the channel spacing, $d_{channel}$.

$$v_{electric} = d_{channel}/t_{ramp} \quad \text{Equation 1:}$$

Therefore, the duration of the current ramps can be adjusted to change the velocity of a dynamic stimulation pulse. In the case of mimicking an acoustic traveling wave, longer duration current ramps are used when a dynamic stimulation pulse nears the location in the cochlea corresponding to the characteristic frequency, and shorter duration current ramps are used elsewhere.

FIG. 8 illustrates an example in which contiguous channels are used to deliver a biphasic dynamic stimulation pulse having a varying velocity in accordance with embodiments presented herein. More specifically, FIG. 8 includes ten traces 188(1)-188(10) that each illustrate the unscaled current waveforms for each of Ch1 through Ch10, respectively, with respect to increasing time. Therefore, the collective traces 188(1)-188(10) represent the delivered dynamic stimulation pulse 195 as a series ramped and damped current segments.

As represented by dashed line 194, the duration of the current ramps are the same in the current waveforms for Ch1 through Ch7 (shown from trace 188(1) to trace 188(7)). As such, the dynamic stimulation pulse 195 has a substantially constant velocity as it moves from Ch1 through Ch7. However, as shown between traces 188(7) and 188(8), the duration of the current ramp slows between Ch7 and Ch8, meaning that the velocity of the dynamic stimulation pulse 195 slows between Ch7 and Ch8. The duration of the current ramps in current waveforms Ch9 and Ch10 are the same as those in Ch1 through Ch7, meaning that, after slowing down between Ch7 and Ch8, the dynamic stimulation pulse 195 returns to the same velocity as in Ch1 through Ch7 (i.e., the dynamic stimulation pulse slows down, but then returns to the original speed).

FIG. 8 also includes a trace 189 representing the sum of the currents from traces 188(1)-188(10). Similar to the above arrangements, since the dynamic stimulation pulse 195 is biphasic, the dynamic current pulse generally is comprised of a charge accumulation phase 190 followed by a subsequent charge balancing phase 192 (i.e., positive phase sweep followed by a negative single phase sweeping across the ten stimulation channels).

Ideally, it is desirable for stimulation channels to stimulate only a narrow region of spiral ganglion neurons such that the resulting neural responses from neighboring stimulation channels have minimal overlap. However, monopolar stimulation typically exhibits a much higher degree of overlap such that a target neuron population may be excited by several different monopolar channels (i.e., stimulation channels delivering monopolar stimulation). Other types of stimulation, including bipolar, tripolar, focused multi-polar ((FMP), a.k.a. "phased-array") stimulation, etc. typically reduce the size of an excited neural population. In accordance with embodiments presented, these or other types of stimulation may be used to generate a dynamic stimulation pulse. The use of, for example, focused multipolar stimulation to generate a dynamic stimulation pulse may allow for a better-defined traveling wave whereas the current spread and wide excitation patterns of monopolar stimulation may, in many cases, obscure the movement of the locus of stimulation. The same principals as described above in which a single pulse is moved along a plurality of stimulation channels may be applied with any of the above or other types of stimulation. However, with focused multipolar stimulation, the activation width may be limited and may provide advantageous characteristics.

In cochlear implants, there are three stimulus characteristics that are typically used to change the perception of stimulation signals through their three neural codes. These stimulus characteristics include: (1) changing the location at which a stimulation pulse is delivered (the place code), (2) changing the rate of stimulation so that the recipient can hear different pitches (even at the same location) (the rate code), or (3) changing the amplitude of the stimulation pulse (the amplitude code). However, a possible fourth neural code is sometimes referred to as the "ensemble code." The ensemble code refers to the idea that, within a short time frame, there is information encoded in the order of stimulation pulses. The very basic theory states that the brain (neural) firing causes pulses delivered first to appear louder than subsequent pulses. Therefore, changes to the order of how a series of stimulation pulses are delivered to a recipient can affect the recipient's perception of those pulses, even if the other three neural codes (i.e., place, rate, and amplitude) remain the same.

Figure 9B:
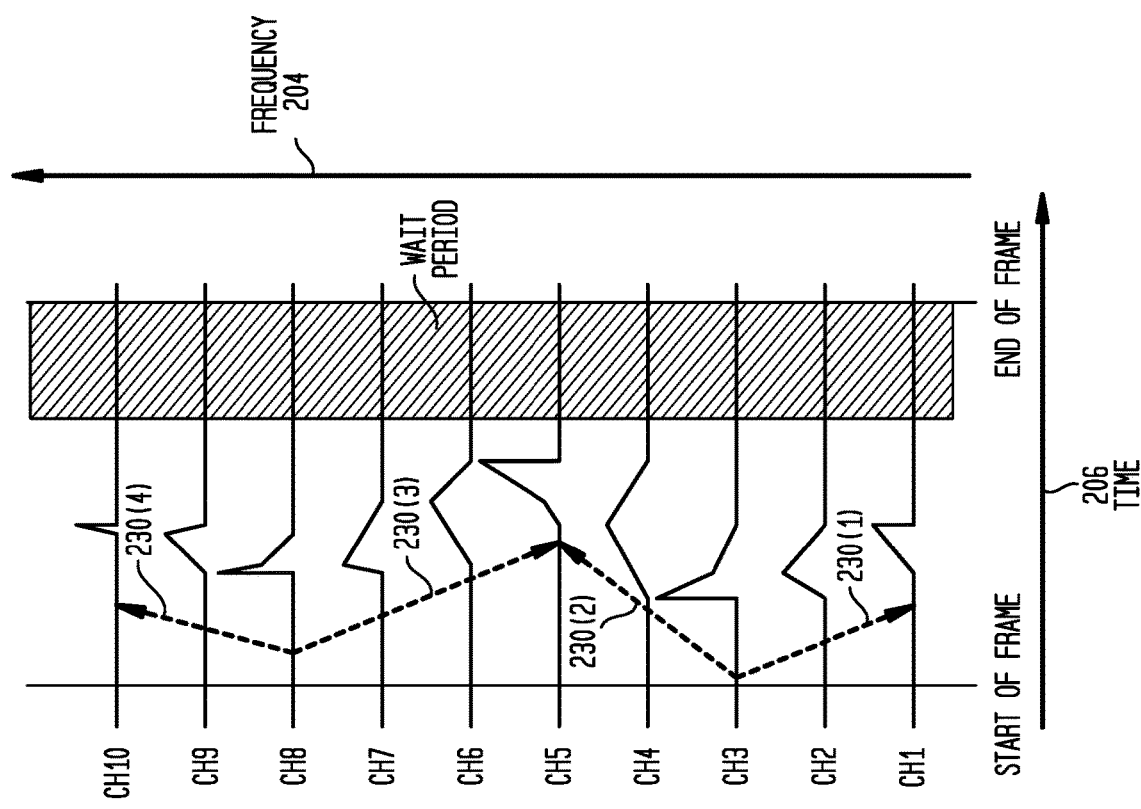
FIG. 9B is a current plot illustrating a plurality of dynamic stimulation pulses generated in response to the PSD of FIG. 9A.
Figure 9A:
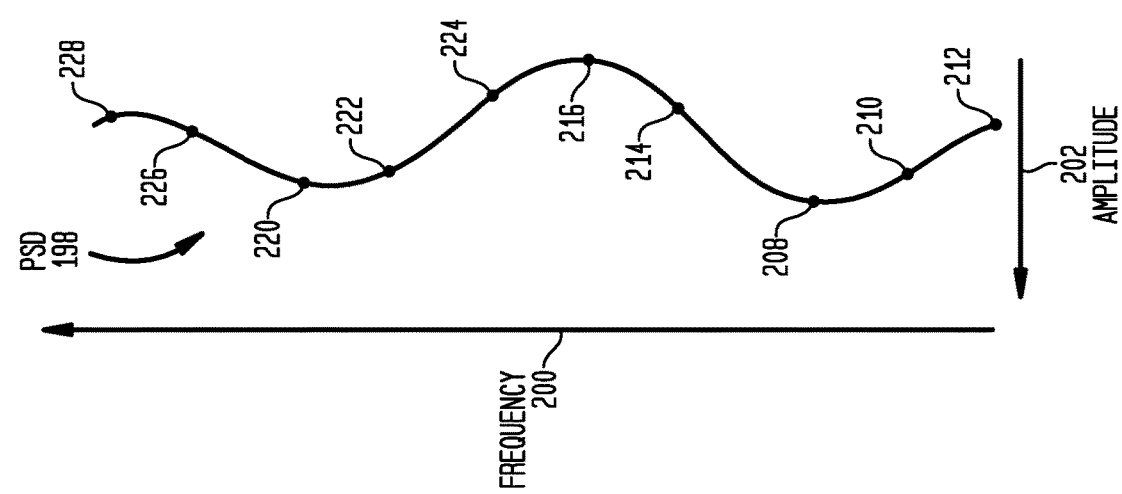
FIG. 9A is a plot of the power spectral density of a sound signal.

In accordance with embodiments presented herein, dynamic stimulation pulses may be used to represent fast ensemble coding features. For example, FIG. 9A illustrates a power spectral density (PSD) 198 for an incoming sound signal. In FIG. 9A, increasing frequency is represented by arrow 200 and increasing amplitude (sound loudness) is represented by arrow 202. FIG. 9B illustrates dynamic stimulation pulses generated in response to the PSD of FIG. 9A. In FIG. 9B, increasing frequency is represented by arrow 204 and increasing time is represented by arrow 206.

As shown, louder portions of the sound signal (as identified as having larger amplitudes in the PSD) are presented on their associated stimulation channel first, and softer sounds are generally presented later. That is, FIG. 9B illustrates the use of amplitude specific delays that result in multiple dynamic stimulation pulses represented by arrows 230(1), 230(2), 230(3), and 230(4) (i.e., four dynamic stimulation pulses formed by groups/sets of ramped and damped current segments). The order of the stimulation channels across which the dynamic stimulation pulses 230(1), 230(2), 230(3), and 230(4) are presented is based on the PSD amplitudes (i.e., amplitude specific or ensemble delays).

More specifically, FIG. 9B illustrates that dynamic stimulation pulses 230(1) and 230(2) both begin at Ch3 where the stimulation corresponds to amplitude point 208 of PSD 198 (i.e., the loudest part of the incoming sound signal). Dynamic stimulation pulse 230(1) is applied across Ch3, Ch2, and Ch1, where the stimulation corresponds to amplitude points 210 and 212, in addition to amplitude point 208. Similarly, dynamic stimulation pulse 230(2) is applied across Ch3, Ch4, and Ch5, where the stimulation corresponds to amplitude points 214 and 216, in addition to amplitude point 208.

FIG. 9B also illustrates that the dynamic stimulation pulses 230(3) and 230(4) both begin at Ch8 where the stimulation corresponds to amplitude point 220 of PSD 198 (i.e., the second loudest peak of the incoming sound signal). Dynamic stimulation pulse 230(3) is applied across Ch8, Ch7, Ch6, and Ch5, where the stimulation corresponds to amplitude points 222, 224, and 216, in addition to amplitude point 220. Similarly, dynamic stimulation pulse 230(4) is applied across Ch8, Ch9, and Ch10, where the stimulation corresponds to amplitude points 226 and 228, in addition to amplitude point 220. As shown, dynamic stimulation pulses 230(3) and 230(4) begin while dynamic stimulation pulses 230(1) and 230(2) are still being delivered.

In general, the amplitude specific delays (ensemble) shown in FIG. 9B are amplitude specific. However, the delays could also or alternatively relate to other parameters such as, for example, phase, fine temporal structure, patient-specific parameters, and/or a combination thereof.

FIG. 9B illustrates several aspects of dynamic stimulation pulses in accordance with embodiments presented herein. First, it can be seen in FIG. 9B that multiple dynamic stimulation pulses may be delivered at the same time, and may simultaneously begin or end on the same channels. Second, FIG. 9B makes it clear that the dynamic stimulation pulses may move in an apical/distal direction (e.g., dynamic stimulation pulses 230(2) and 230(4)) or in a basal/proximal direction (e.g., dynamic stimulation pulses 230(1) and 230(3)). Third, FIG. 9B illustrates that the dynamic stimulation pulses 230(1), 230(2), 230(3), and 230(4) may travel at different velocities (i.e., the location of the locus of stimulation may change at different rates) and that the velocity of a single dynamic stimulation pulse may change as it traverses different stimulation channels.

Figure 10B:
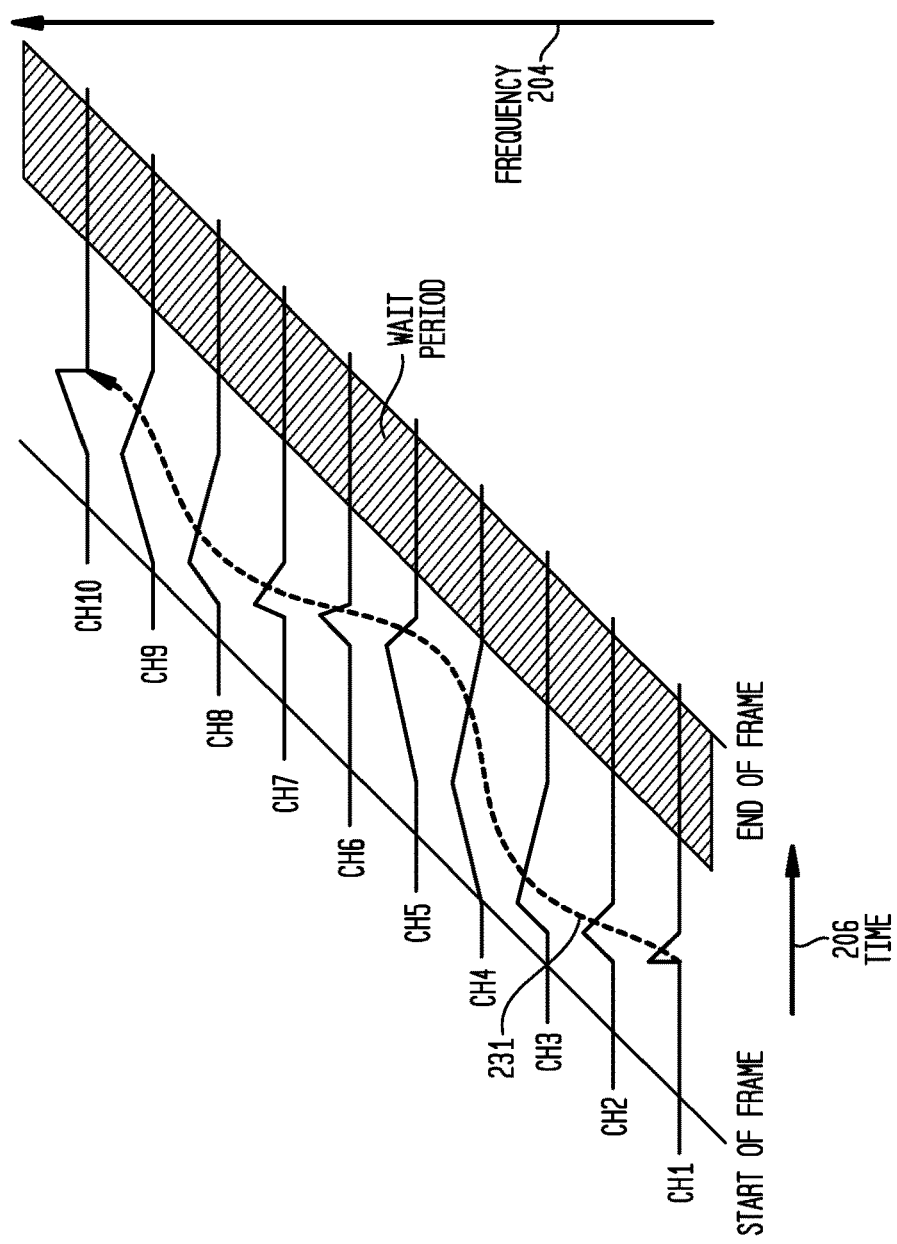
FIG. 10B is a current plot illustrating a plurality of dynamic stimulation pulses generated in response to the PSD of FIG. 10B.
Figure 10A:
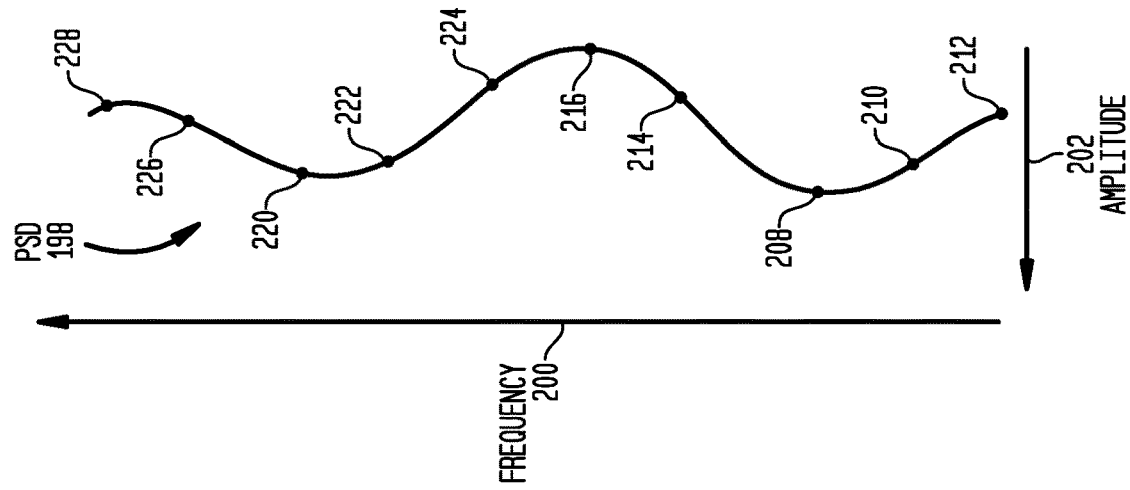
FIG. 10A is a plot of the power spectral density of a sound signal.

As noted above, the acoustic traveling wave moves distally/apically from the basal end of the cochlea towards the characteristic frequency of the stimulus. The delay along the cochlea of the acoustic travelling wave is approximately 10 ms. Assuming, for simplification, that the travelling wave speed is constant and that stimulation channels are evenly spaced, then a 10 ms delay spread across twenty (20) stimulation channels is approximately 500 µs between two consecution stimulation channels. This delay may be used in combination with the ensemble encoding strategy to better recreate the natural travelling wave effect. That is, further timing delays or advancements could be added to the expected dynamic pulse time depending on their frequency specific amplitude. This would be to delay or advance the neural activation compared to a constantly travelling sliding pulse. For instance, a delay of possibly half the expected transition length (120 µs) could be added to pulses at low levels, and scaled up to no delay for pulses at high levels. FIGS. 10A and 10B illustrate an example for using the acoustic traveling wave delay in combination with the ensemble code.

FIG. 10A again illustrates PSD 198 plotted as amplitude versus frequency. FIG. 10B illustrates a dynamic stimulation pulse 231 generated in response to the PSD 198 of FIG. 10A. In FIG. 10B, increasing frequency is represented by arrow 204 and increasing time is represented by arrow 206.

As noted, the stimulation pulse 231 is generated from the same PSD 198 as the stimulation pulses 230(1)-230(4) of FIG. 9B. However, in the embodiment of FIG. 10B, the start of the stimulation at each channel is time dependent. More specifically, in FIG. 9B the start of the stimulation at each channel corresponds to the same point in time (same time point). In contrast, in FIG. 10B the stimulation is progressively delayed at each subsequent channel so as to follow the frequency specific time delays related to the travelling wave (or at least a linear graphical representation thereof).

In addition to the frequency specific delays (travelling wave), FIG. 10B also illustrates use of the same amplitude specific delays (ensemble delays) that are also shown in FIG. 9B. That is, the louder signals in the PSD 198 are presented closer to the start of the stimulation frame in both cases. However, since FIG. 10B also includes the frequency specific delays (travelling wave delays), the resulting dynamic stimulation pulse(s) is/are different from pulses 230(1)-230(4) of FIG. 9B. That is, instead of the different sliding pulses with different directions as shown in FIG. 9B, when the amplitude specific delays are added to the frequency specific delays as shown in FIG. 10B, the result is a single dynamic stimulation pulse (i.e., single sliding pulse) 231.

As noted, FIG. 10A illustrates an example with a single dynamic stimulation pulse 231. Other embodiments may result in a number of different sliding pulses travelling in the same direction as pulse 231.

FIG. 11 is a flowchart of a method 350 in accordance with embodiments presented herein. Method 350 begins at 352 where a tissue-stimulating prosthesis system, such as a cochlear implant system, sound processor receives one or more sound signals. At 352, the sound processor processes the one or more sound signals to determine at least one stimulation pulse representative of the one or more sound signals. At 354, the at least one stimulation pulse is delivered to the recipient as current stimulation that is applied via a plurality of stimulation channels such that a location of a locus of the current stimulation progresses over time across the plurality of channels.

FIG. 12 is a flowchart of another method 360 in accordance with embodiments presented herein. Method 360 begins at 362 where a tissue-stimulating prosthesis system, such as a cochlear implant system, sound processor receives an input audio signal. At 364, the tissue-stimulating prosthesis system generates, based on the input audio signal, a series of pulse amplitudes. At 366, for the duration of a first transition period, a first pulse amplitude in the series of pulse amplitudes is divided into first and second divided portions.

The first and second divided portions of the first pulse amplitude sum to the first pulse amplitude, and the first and second divided portions of the first pulse amplitude change at a first rate with opposite polarities, respectively. At 368, first stimulation current is generated based on the first divided portion and the first stimulation current is delivered to a recipient via a first stimulation channel. At 370, second stimulation current is generated based on the second divided portion and the second stimulation current is delivered to the recipient via a second stimulation channel.

In one embodiment, a method is provided. The method comprises receiving an input audio signal; generating, based on the input audio signal, a series of pulse amplitudes; dividing, for a duration of a first transition period, a first pulse amplitude in the series of pulse amplitudes into first and second divided portions, wherein the first and second divided portions of the first pulse amplitude sum to the first pulse amplitude, and wherein the first and second divided portions of the first pulse amplitude change at a first rate with opposite polarities, respectively; generating first stimulation current based on the first divided portion and delivering the first stimulation current to a recipient via a first stimulation channel; and generating second stimulation current based on the second divided portion and delivering the second stimulation current to the recipient via a second stimulation channel. In one example, the first rate is constant while in another example the first rate is variable. In one example, the first and second stimulation channels are adjacent channels in a series of stimulation channels. In another example, the first and second stimulation channels are separated by a third stimulation channel in the series of stimulation channels. In one example, the method further comprises dividing, for a duration of a second transition period, a second pulse amplitude in the series of pulse amplitudes into third and fourth divided portions, wherein the third and fourth divided portions of the second pulse amplitude sum to the second pulse amplitude, and wherein the third and fourth divided portions of the second pulse amplitude change at a second rate with opposite polarities, respectively; generating third stimulation current based on the third divided portion and delivering the third stimulation current to the recipient via a third stimulation channel; and generating fourth stimulation current based on the fourth divided portion and delivering the fourth stimulation current to the recipient via a fourth stimulation channel. In one example, the first and second pulse amplitudes are equal while in another example the first and second pulse amplitudes are unequal. In one example, the first and second rates are equal while in another example the first and second rates are unequal.

It is to be appreciated that the above embodiments are not mutually exclusive and may be combined with one another in various arrangements.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. An apparatus, comprising:
   one or more sound input elements configured to receive one or more sound signals;
   at least one sound processor configured to generate one or more processed signals representative of the one or more sound signals;
   a plurality of stimulation channels each terminating at one or more electrical stimulating contacts implantable in a recipient; and
   a stimulator arrangement configured to simultaneously generate, based on at least one of the one or more processed signals, overlapping time varying current fields representative of at least one of the one or more sound signals across at least first and second stimulation channels of the plurality of stimulation channels that collectively result in a time varying change in a locus of the overlapping time varying current fields,
   wherein the stimulator arrangement is configured to dynamically split current between the first stimulation channel and the second stimulation channel, and to control instantaneous amplitudes of the overlapping time varying current fields based on one or more attributes of the at least one of the one or more sound signals, such that a location of the locus of the overlapping time varying current fields progresses over time from the first stimulation channel to the second stimulation channel,
   wherein the stimulator arrangement is configured to dynamically vary a rate of change of the location of the locus of the overlapping time varying current fields at one or more locations between the first stimulation channel and the second stimulation channel based on one or more attributes of the one or more sound signals.

2. The apparatus of claim 1, wherein the one or more electrical stimulating contacts are part of a stimulating assembly configured to be implantable in a cochlea of the recipient.

3. The apparatus of claim 1, wherein the stimulator arrangement is configured to vary an amplitude of the current that is dynamically split between the first stimulation channel and the second stimulation channel to cause changes in the amplitude of the locus of the overlapping time varying current fields at one or more locations between the first stimulation channel and the second stimulation channel as the location of the locus progresses from the first stimulation channel to the second stimulation channel.

4. The apparatus of claim 1, wherein the stimulator arrangement is configured to vary an amplitude of the current that is dynamically split between the first stimulation channel and the second stimulation channel to cause changes in the rate of change of the location of the locus of the overlapping time varying current fields at one or more locations between the first stimulation channel and the second stimulation channel as the location of the locus progresses from the first stimulation channel to the second stimulation channel.

5. The apparatus of claim 1, wherein the locus of the overlapping time varying current fields moves in a linear manner between a first location at the first stimulation channel and a second location at the stimulation second channel.

6. The apparatus of claim 1, wherein the locus of the overlapping time varying current fields moves in a continuously varying manner between a first location at the first stimulation channel and a second location at the stimulation second channel.

7. The apparatus of claim 1, wherein the stimulator arrangement is configured to dynamically change a weighting of the current that is dynamically split between the first stimulation channel and the second stimulation channel such that the location of the locus of the overlapping time varying current fields gradually shifts from the first stimulation channel to the second stimulation channel over time.

8. The apparatus of claim 7, wherein the weighting of the current changes in an inverse linear manner such that the weighting applied at the first stimulation channel linearly decreases over time and the weighting applied at the second stimulation channel linearly increases over time.

9. The apparatus of claim 1, wherein the overlapping time varying current fields representative of the one or more sound signals are associated with a specific acoustic frequency range, and wherein the stimulator arrangement is configured to reduce the amplitude of the current to cause the rate of change of the location of the locus to be reduced at or near a location corresponding to the specific acoustic frequency range.

10. A method, comprising:
receiving one or more sound signals at an auditory prosthesis system;
determining a first stimulation pulse representative of the one or more sound signals; and
delivering the first stimulation pulse as first and second current signals, substantially simultaneously applied at first and second stimulation channels, respectively,
wherein the first and second current signals are dynamically split between the first and second stimulation channels to generate overlapping time varying current fields representative of the one or more sound signals across the first and second stimulation channels, and are dynamically weighted based on one or more attributes of the one or more sound signals, so as to substantially continually move a location of a locus of the first stimulation pulse over time between a first location at the first stimulation channel and a second location at the second stimulation channel,
wherein a rate of change in the movement of the location of the locus of the overlapping time varying current fields is dynamically varied at one or more locations between the first stimulation channel and the second stimulation channel based on one or more attributes of the one or more sound signals.

11. The method of claim 10, further comprising:
receiving one or more environmental signals at the auditory prosthesis system; and
processing the one or more environmental signals to determine the first stimulation pulse representative of the one or more environmental signals.

12. The method of claim 10, wherein the first and second current signals are dynamically weighted relative to one another in order to, during delivery of the first stimulation pulse, move the location of the locus of the first stimulation pulse from the first location at the first stimulation channel to the second location at the second stimulation channel.

13. The method of claim 10, further comprising:
varying, at one or more locations between the first location at the first stimulation channel and the second location at the second stimulation channel, an amplitude of the locus of the first stimulation pulse based on amplitudes of the one or more sound signals.

14. The method of claim 13, wherein varying an amplitude of the locus of the first stimulation pulse further comprises:
varying, an amplitude of the locus of the first stimulation pulse based on the amplitudes of the one or more sound signals and one or more recipient-specific factors.

15. The method of claim 10, further comprising:
varying, at one or more locations between the first location at the first stimulation channel and the second location at the second stimulation channel, a rate at which the location of the locus of the first stimulation pulse moves between the first location at the first stimulation channel and the second location at the second stimulation channel.

16. The method of claim 15, wherein the first stimulation pulse representative of the one or more sound signals is associated with a specific acoustic frequency range, and wherein the method further comprises:
reducing, at a third location corresponding to the specific acoustic frequency range, the rate of at which the location of the locus of the first stimulation pulse moves between the first location at the first stimulation channel and the second location at the second stimulation channel.

17. The method of claim 10, wherein the locus of the first stimulation pulse moves in a linear manner between the first location at the first stimulation channel and the second location at the second stimulation channel.

18. The method of claim 10, wherein the locus of the first stimulation pulse moves in a continuously varying manner between the first location at the first stimulation channel and the second location at the second stimulation channel.

19. The method of claim 10, wherein the first stimulation channel and the second stimulation channel are separated by one or more other stimulation channels.

* * * * *